United States Patent [19]

Shoesmith

[11] Plant 5,027

[45] Apr. 5, 1983

[54] CHRYSANTHEMUM NAMED GLACIER (P6-134-W)

[75] Inventor: Leonard H. Shoesmith, Westfield-Woking, England

[73] Assignee: Pan American Plant Co., Parrish, Fla.

[21] Appl. No.: 312,886

[22] Filed: Oct. 19, 1981

[51] Int. Cl.[3] ..... A01H 5/00

[52] U.S. Cl. ..... Plt./77

[58] Field of Search ..... Plt./77

*Primary Examiner*—Robert E. Bagwill

*Attorney, Agent, or Firm*—Chas. W. Rummler

[57] ABSTRACT

A new and distinct decorative type chrysanthemum of an overall creamy white color having medium sized blooms with very many spoon-tipped ray florets, a vigorous and upright growth habit and a profuse production of medium sized blooms. This variety will not pink under cool temperatures nor delay under high temperature conditions.

4 Drawing Figures

BACKGROUND OF THE NEW PLANT

This new chrysanthemum variety originated as a seedling of unknown parentage discovered by me among a field of miscellaneous seedlings grown in greenhouse at West Chicago, Ill., with the object of finding new and favorable varieties for pot plant production. This plant was selected for trial because of its almost standard shape and its overall creamy white color and the discovery plant was propagated under my direction, by means of cuttings, at West Chicago, Ill., and the results being favorable, this new variety was then propagated through successive generations, which determined that its novel characteristics would hold true from generation to generation and that such characteristics appeared to be firmly fixed. The tests of this new plant having proved to be satisfactory, commercial scale propagation of this new plant was begun at Parrish and Cortez, Fla., as well as at West Chicago, Ill., such propagation being carried on by means of cuttings.

DESCRIPTION OF THE DRAWINGS

This new chrysanthemum cultivar is illustrated by the accompanying drawings, of which sheet one is a full color photographic rendition of a full grown potted plant showing its general form at maturity and the nature of its blooms; sheet two is a photographic print of a close-up face view of several flowers of this new variety which has been hand painted to show the true coloration of the blooms; sheet three is a print of a mechanical reproduction of the front side of typical leaves of this new plant; and sheet four is a similar print showing the back or under side of the leaves pictured on sheet three.

DESCRIPTION OF THE NEW PLANT

The following is a detailed description of my new chrysanthemum variety based upon observations of greenhouse grown plants made in the Spring of 1981, the color designations being according to The R.H.S. Colour Chart published by The Royal Horticultural Society of London, England.

THE PLANT

Origin: Seedling.
Parentage: Unknown.

Classification:
- *Botanic.*—*Chrysanthemum morifolium.*
- *Commercial.*—Pot Chrysanthemum.

Form: Herbaceous bush.
Height: Varies according to cultural treatment.
Growth: Vigorous, strong and upright.
Growth rate: Rapid.
Branching character: Caespitose under normal conditions.
Foliage:
- *Quantity.*—Abundant.
- *Size of leaf.*—From insignificant to about 70 mm. long and to about 65 mm. wide.
- *Shape of leaf.*—Ovate with cleft margin.
- *Texture.*—Leathery.
- *Ribs and veins.*—Pinnate.
- *Color.*—Upper side — 147A. Under side — 147B.
- *Petioles.*—Of various lengths.
- *Rachis.*—About 40 to 70 mm. long.
- *Leaflets.*—Very few in number and of various sizes.

THE BUD

Shape: Globular.
Size: Variable in both diameter and length.
Opening rate: Typical chrysanthemum.
Color of florets:
- *When phyllaries first divide.*—155A.
- *When petals begin to unfurl.*—155D.

Phyllaries:
- *Number.*—About 13.
- *Shape.*—Lanceolate.
- *Color.*—148C.

Peduncle:
- *Character.*—Rigid and erect.
- *Length.*—Varies.
- *Surface aspect.*—Pubescent.
- *Color.*—148C.

THE FLOWER

Blooming habit: Intermittent and blooms profusely.
Blooms:
- *Size.*—Medium. Diameter — About 70 to 100 mm. Depth — About 20 to 30 mm.
- *Borne.*—Cyme.
- *Form.*—A decorative type inflorescence of spoon-tipped ray florets borne on a receptacle surrounded by an involucre of bracts.

*Shape.*—When bloom first opens — Cup-shaped. When bloom matures — Flattened.

Petalage:

*Florets.*—Many ray florets; few disc florets.

*Arrangement.*—Imbricated.

*Form.*—Lanceolate with rounded apex and entire margin.

Texture: Soft.

Appearance: Satiny.

Color:

*Outer florets.*—Front side — 155D. Back side — 155D. Inside florets at the center of the bloom go from creamy white to pale yellow to green in the very center of the blossom.

Peduncle:

*Length.*—Varies.

*Character.*—Strong and upright.

*Color.*—148C.

Persistence: Florets hang on and dry.

Fragrance: Typical chrysanthemum.

Lasting quality:

*On plant.*—3 to 4 weeks.

*As cut flower.*—Not recommended.

REPRODUCTIVE ORGANS

Stamens:

*Arrangement.*—Syngenesious.

*Number.*—Five.

*Anthers.*—Size: Insignificant. Color: Yellow.

*Filaments.*—Length: Insignificant. Color: Yellow.

*Pollen.*—Color — Yellow.

Pistils:

*Number.*—One for each floret.

*Styles.*—Length: Insignificant. Color: Yellow.

Stigmas:

*Color.*—Yellow.

Ovaries: Inferior; bicarpellate.

This new chrysanthemum has an excellent growth habit and its creamy white blooms provide an exceedingly attractive appearance above an abundant display of dark green foliage. This plant is at its best from April through November but may be flowered the year around under high light conditions. This variety will not pink under cool temperatures or delay under high temperatures and is an excellent variety for pot plant culture.

I claim:

1. A new and distinctive chrysanthemum cultivar, substantially as herein shown and described, particularly characterized by the creamy white coloration of its generally standard type blooms, its vigorous growth habit and its high production of medium sized flowers.

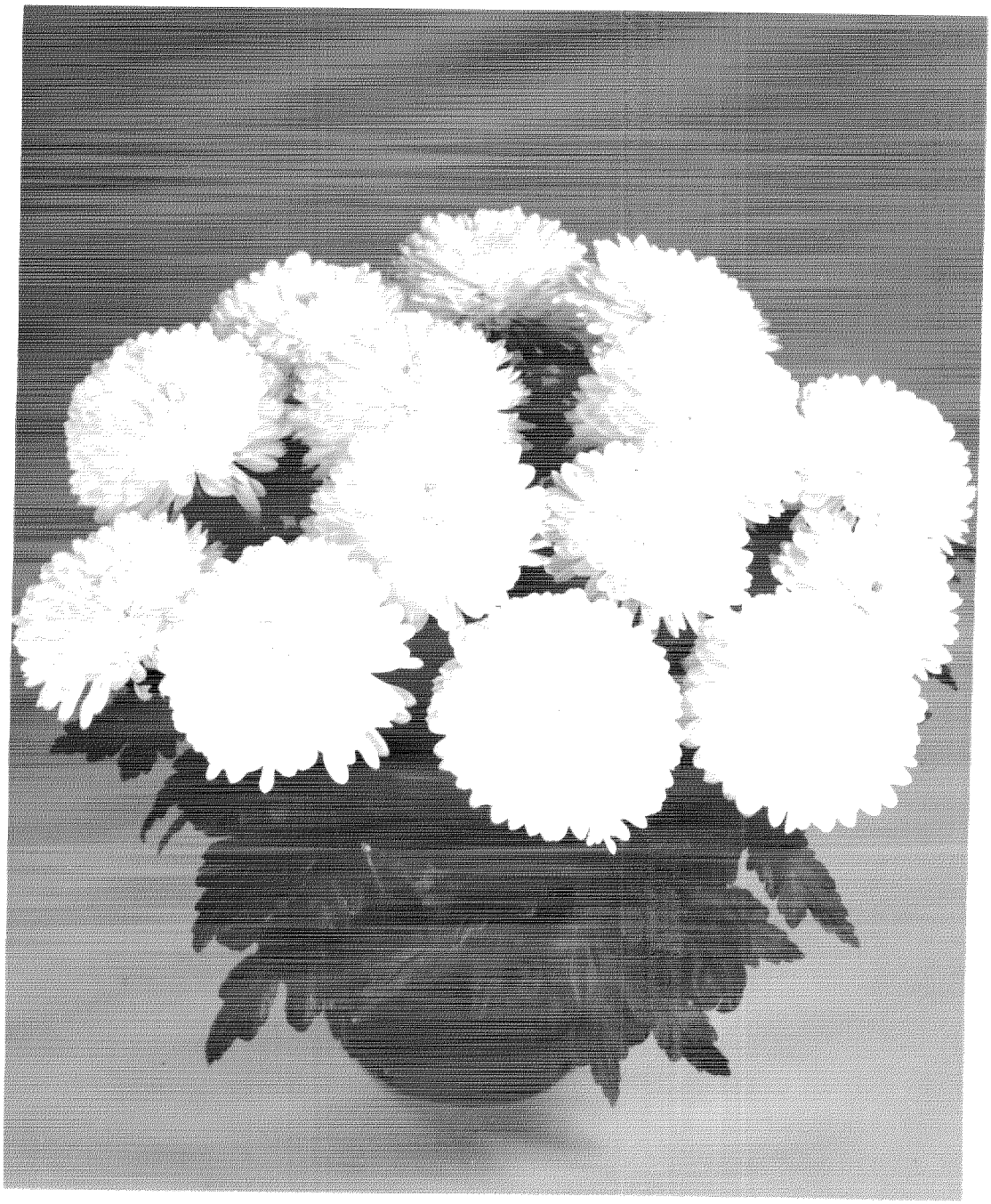

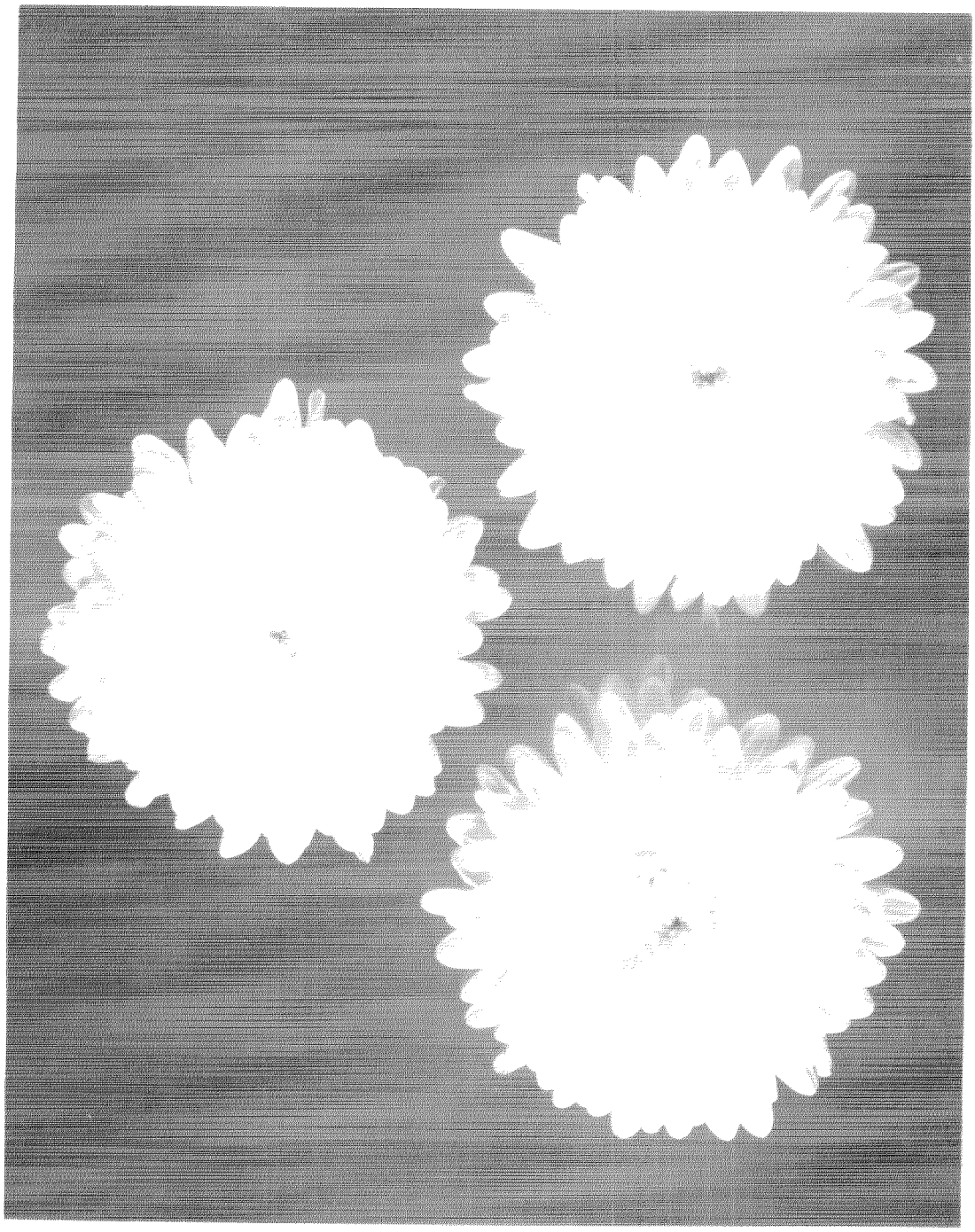

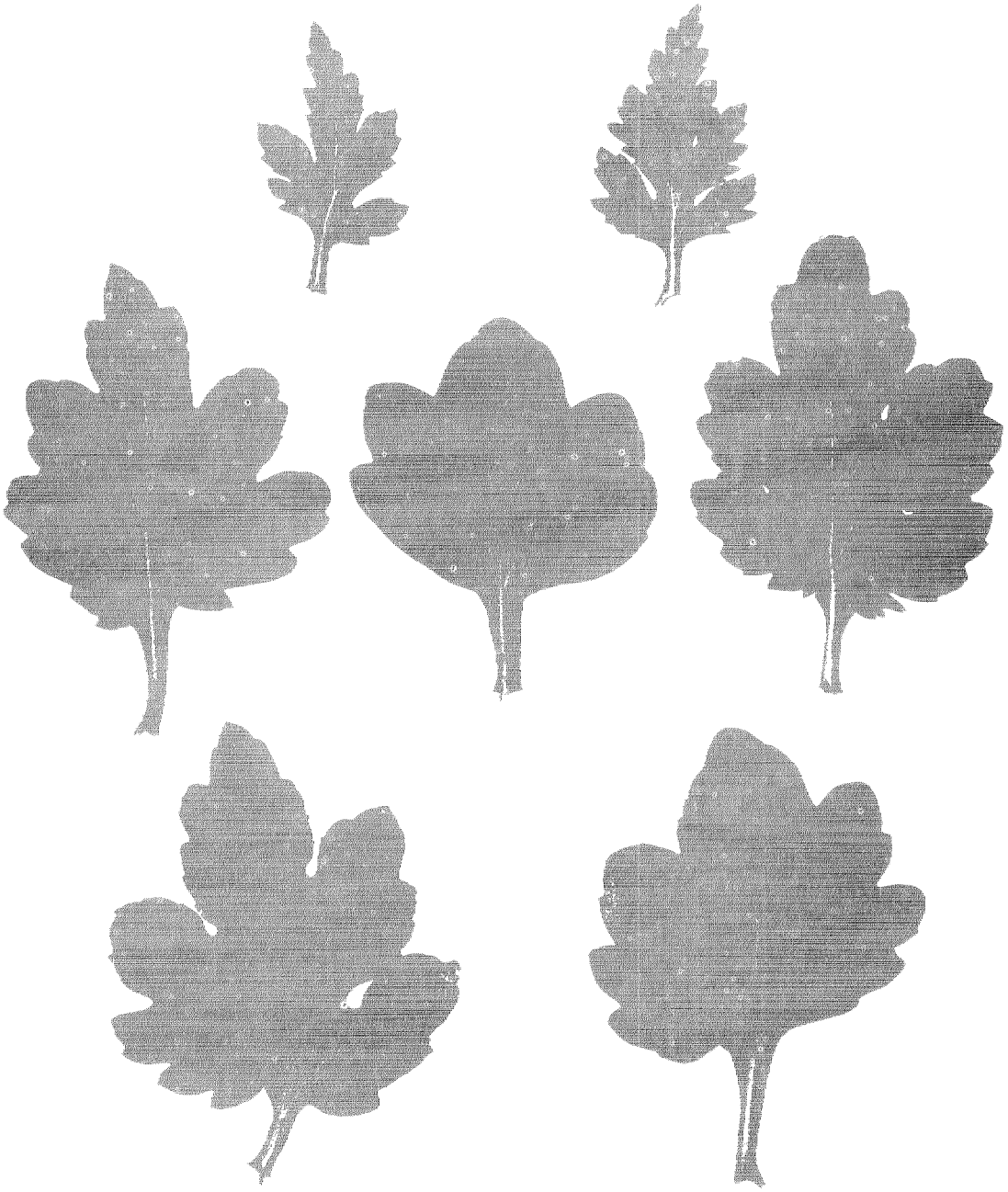

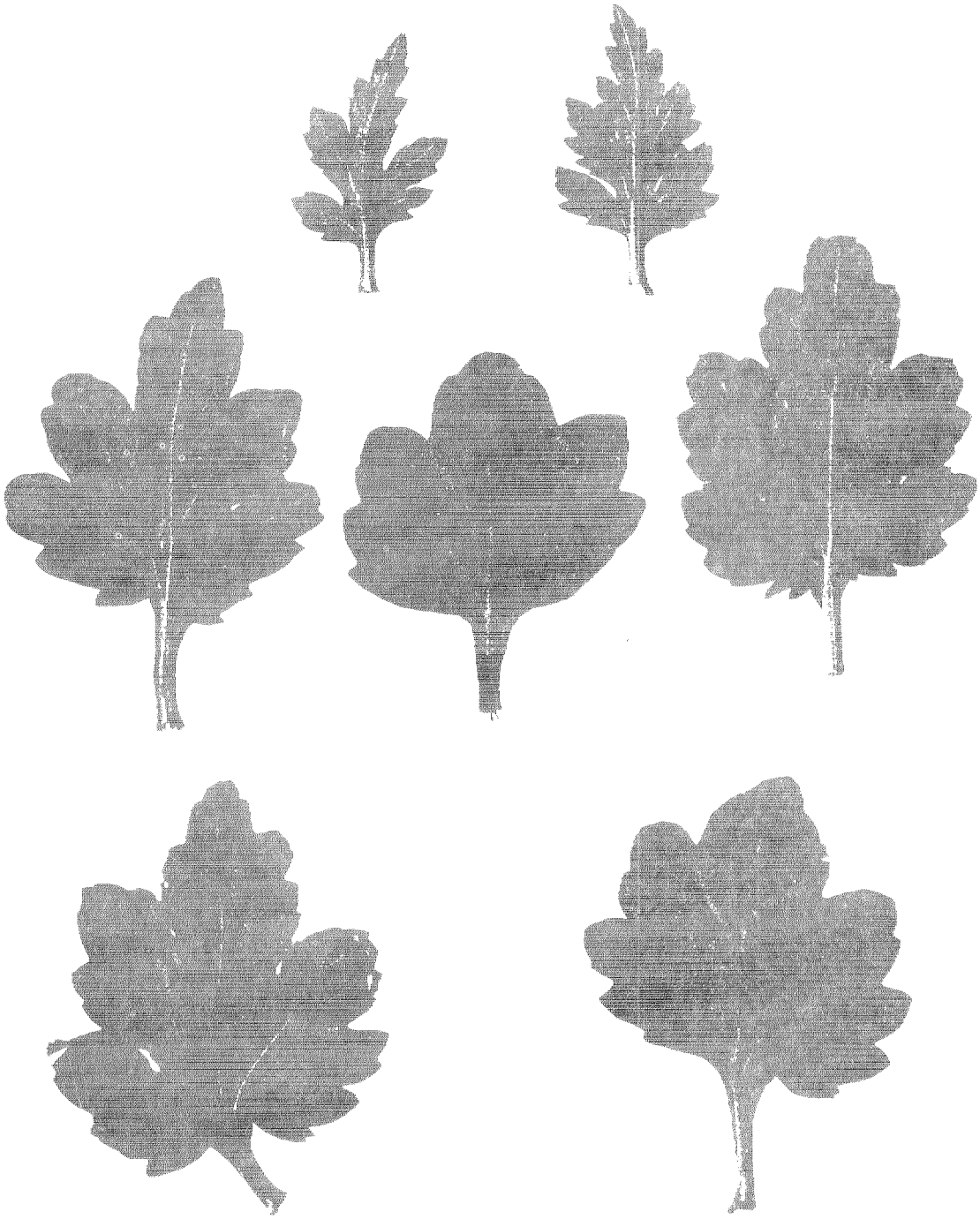

* * * * *